United States Patent

Matsumoto et al.

Patent Number: 5,354,653
Date of Patent: Oct. 11, 1994

[54] METHOD OF TYPE-SPECIFIC DETECTION OF HERPES SIMPLEX VIRUS

[75] Inventors: Toshiya Matsumoto, Tokyo; Takashi Kurimura, Hyogo; Hiroshi Kita, Tokyo, all of Japan

[73] Assignee: Iatron Laboratories, Inc., Tokyo, Japan

[21] Appl. No.: 949,488
[22] PCT Filed: Feb. 24, 1992
[86] PCT No.: PCT/JP92/00196
§ 371 Date: Oct. 22, 1992
§ 102(e) Date: Oct. 22, 1992
[87] PCT Pub. No.: WO92/14846
PCT Pub. Date: Sep. 3, 1992

[30] Foreign Application Priority Data
Feb. 25, 1991 [JP] Japan ................... 3-53336

[51] Int. Cl.$^5$ ............ C12Q 1/70; C12P 19/34; C07H 21/04
[52] U.S. Cl. .................. 435/5; 435/6; 435/91.2; 536/24.32; 536/24.33; 935/77; 935/78; 935/17
[58] Field of Search .......... 435/6, 5, 91, 91.2; 536/24.32, 24.33; 935/77, 78

[56] References Cited
FOREIGN PATENT DOCUMENTS
0326395 1/1989 European Pat. Off. .
WO9100363 1/1991 World Int. Prop. O. .

OTHER PUBLICATIONS
Davison et al. J ger Virol (1981) 55: 315–331.
Kimura Med Microbiol Immunol (1990) 179: 177–184.
McGeoch et al. J. Ger Virol (Dec. 1991) 72: 3057–3075.
McGeoch et al. J. Gen Virol (1988) 69: 1531–1574.
Vandenwelde et al. J. Virol Methods (1990) 30: 215–228.

*Primary Examiner*—Margaret Parr
*Assistant Examiner*—Carla Myers
*Attorney, Agent, or Firm*—Sherman and Shalloway

[57] ABSTRACT

The present invention relates to a method of the type-specific detection of herpes simplex virus, characterized by comprising the step of DNA amplification in a liquid mixture containing either of a combination of a first DNA primer containing an oligonucleotide having at least 15 bases in a base sequence of the formula (1a)

CACGGGTATA AGGACATCCA (SEQ ID NO: 1)     (1a)

with a second DNA primer containing an oligonucleotide having at least 15 bases in a base sequence of the formula (2a):

GGGTCCTCGT CCAGATCGCT (SEQ ID NO: 2),     (2a)

or a combination of a first DNA primer containing an oligonucleotide having at least 15 bases in a base sequence of the formula (1b):

GCCTCTTTTC CCCCGGGGAG (SEQ ID NO: 3)     (1b)

with a second DNA primer containing an oligonucleotide having at least 15 bases in a base sequence of the formula (2b):

GGGAAAAAAG CCGCGCCGGGG (SEQ ID NO: 4),     (2b)

a DNA polymerase and an aqueous liquid sample; and then the step of DNA examination on the resultant reaction solution.

According to the present invention, it is possible to differentiate infectious disease caused by the HSV I or HSV II, accurately and rapidly in a type specific manner.

17 Claims, 2 Drawing Sheets

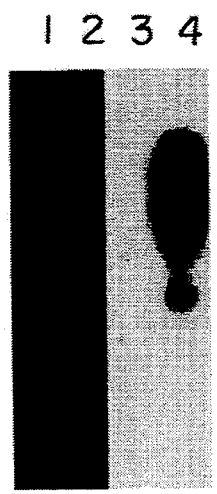

METHOD OF TYPE-SPECIFIC DETECTION OF HERPES SIMPLEX VIRUS

TECHNICAL FIELD

The present invention relates to a method of the type-specific detection of the human herpes simplex virus Type I (hereinafter optionally referred to as HSV I) and the human herpes simplex virus Type II (hereinafter optionally referred to as HSV II).

BACKGROUND ART

Human herpes simplex virus (HSV) lies dormant in the human sensory ganglions. Once one is infected, the disease recurs repeatedly. There are two types in HSV: Type I and Type II. The rate of recurrence and the sensitivity to drugs differ depending on the type. Therefore, the determination of the type of HSV is important. The most reliable method of diagnosis of the HSV infectious disease is to isolate the virus for determination, but this method requires culture cells and requires several days for the determination, so is difficult to appropriately reflect the results in treatment. There is also a method of determination using a fluorescent antibody, but in this case cells of the diseased area are required. Further, there is known a method of using DNA fragments type-specific to HSV as a probe and examining a sample of the patient by the dot blot method. Nevertheless, this method does not only require a lot of sample (for example, 200 to 500 $\mu$l), but also was not able to determine the type of HSV, even when HSV was found. Therefore, there has been a desire for the development of a technique and in vitro diagnostic agents which enable determination of HSV I and HSV II with high precision in a short time.

On the other hand, while it had been said in the past that there was no base sequence which would enable type-specific recognition of HSV, the present inventors have already developed a type-specific DNA probe for HSV. Namely, it is possible to obtain a type-specific DNA probe by labeling DNA fragments obtained by cleaving HSV I or HSV II DNA with particular restriction enzymes [or DNA fragments obtained by cleaving DNA obtained by inserting the DNA fragments into an appropriate vector (plasmid) and cloning the same, with particular restriction enzymes]. These labeled DNA fragments include several hundred to several thousand bp (base pairs) and are superior in type-specificity. Details thereof are disclosed in Japanese Unexamined Patent Publication No. 2-142499 and Japanese Patent Application No. 2-90198.

However, the above-mentioned labeled DNA fragments have a size difficult to prepare by chemical synthesis. Therefore, the present inventors engaged in further studies to discover base sequence which can be easily handled (for example, a size to an extent that chemical synthesis can be adopted) without reducing type-specificity. As a result, a relatively small base sequence which can be used in type-specific determination was discovered. Namely, the object of the present invention is to provide various primers which can be used for the amplification of DNA fragments specific to HSV I or HSV II, and probes specific to HSV I DNA or HSV II DNA.

DISCLOSURE OF INVENTION

Accordingly, the present invention relates to a method of the type-specific detection of herpes simplex virus, characterized by comprising the step of DNA amplification in a liquid mixture containing either of a combination of a first DNA primer containing an oligonucleotide having at least 15 bases in a base sequence of the formula (1a) ·

CACGGGTATA AGGACATCCA (SEQ ID NO: 1)     (1a)

[hereinafter optionally referred to as the primer (1a)] with a second DNA primer containing an oligonucleotide having at least 15 bases in a base sequence of the formula (2a):

GGGTCCTCGT CCAGATCGCT (SEQ ID NO: 2)     (2a)

[hereinafter optionally referred to as the primer (2a)] or a combination of a first DNA primer containing an oligonucleotide having at least 15 bases in a base sequence of the formula (1b):

GCCTCTTTTC CCCCGGGGAG (SEQ ID NO: 3)     (1b)

[hereinafter optionally referred to as the primer (1b)] with a second DNA primer containing an oligonucleotide having at least 15 bases in a base sequence of the formula (2b):

GGGAAAAAAG CCGCGCCGGGG (SEQ ID NO: 4)     (2b)

[hereinafter optionally referred to as the primer (2b)], a DNA polymerase and an aqueous liquid sample; and then the step of DNA examination on the resultant reaction solution. In the base sequence of the present specification, A denotes an adenine residue, C denotes a cytosine residue, G denotes a guanine residue, and T denotes a thymine residue.

BRIEF DESCRIPTION OF DRAWINGS

FIG. 3 shows the results of confirmation of the electrophoresis images of FIG. 2 by the Southern hybridization method using probes labeled by a radioisotope.

FIG. 4 shows the results of in-situ hybridization using probes of the present invention labeled by a radioisotope.

BEST MODE FOR CARRYING OUT THE INVENTION

Figure 1:
FIG. 1 shows the results of electrophoresis relating to DNA's amplified by a PCR using the HSV I primer of the present invention.

The liquid sample used in the method of the present invention is not particularly limited so far as the sample is suspected of containing HSV. For example, it is possible to use the bulla, throat swab, spinal fluid or the like of patients.

The HSV detection method of the present invention mainly comprises (1) a DNA amplification step and (2) a DNA detection step. In the DNA amplification step (1), it is possible to use the PCR (polymerase chain reaction) method. By the PCR method, it is possible to amplify the desired DNA region automatically from a small amount of DNA to about one million-fold (*Science*, 239, 487 to 491, 1988). In the PCR method, two types of DNA primers are used: a primer for the + (plus) strand (hereinafter referred to as the first primer) and the primer for the − (minus) strand (hereinafter referred to as the second primer) sandwiching the DNA region to be amplified.

As combinations of the first and second primers used in the DNA amplification step (1) of the present invention, there are the following two combinations:

(a) The first primer (1a) and the second primer (2a), and (b) The first primer (1b) and the second primer (2b).

The above combinations (a) and (b) may be used alone or simultaneously. When the combination (a) of the primers is used, it is possible to perform detection specific to HSV I, and when the combination (b) of the primers is used, it is possible to perform detection specific to HSV II.

The base sequences of the formulae (1a) and (2a) lie at the 0.75 map unit on the HSV I DNA gene map. The base sequence of the formula (1a) includes the 20 bases of the complementary strand from the 239th base to the 258th base downstream of the 5' end of the BamHIB fragment, while the base sequence of the formula (2a) includes the 20 bases of the complementary strand from the 48st base to 482nd base downstream from the 5' end of the BamHIB fragment. The base sequences of the formulae (1b) and (2b) lie at the a' sequence of the HSV II DNA (J. Gen. Virol., 55, 315 to 331, 1981). The base sequence of the above-mentioned formula (1b) includes the 20 bases of the complementary strand from the eighth base to the 27th base downstream of the 5' end of the a' sequence, while the base sequence of the above-mentioned formula (2b) includes the 20 bases of the complementary strain from the 219th base to the 200th base downstream from the 5' end of the a' sequence. Therefore, according to the method of the present invention, when HSV I DNA is present in the sample, the combination of the primers (1a) and (2a) amplifies the 243 bp portion corresponding to a part of the BamHI fragment gene, while when HSV II DNA is present in the sample, the combination of the primers (1b) and (2b) amplifies the 212 bp portion corresponding to a part of the a' sequence gene, in the specific manner, in large amounts and a short time, respectively. Accordingly, the presence of HSV I DNA and HSV II DNA in the sample can be detected in the extremely specific manner.

The first and second primers may respectively be 15 mer to 30 mer, but in general 20 mer to 25 mer. If the primers become less than 15 mer, the specificity is reduced upon annealing and nonspecific bonds are increased. Further, if the primers become over 30 mer, secondary structures are liable to occur between the primer molecules or in the molecules. The bases included in the first primer and second primer used in the present invention may be modified by any known manner (for example, biotinated or labeled by a fluorescent substance).

The first and second primers according to the present invention can be prepared by a known DNA synthesis method (for example, the phosphoamidite method) using an ordinary automatic DNA synthesizing apparatus (for example, Applied Biosystems)

In the DNA amplification step (1) of the present invention, the amplification cycle is repeated using a DNA polymerase, particularly a heat resistant DNA polymerase, in addition to the first and second primers.

As the heat resistant DNA polymerase, there may be used a DNA polymerase which can maintain its activity at a temperature up to 95° C., for example, a commercially available Taq polymerase.

In the DNA amplification step of the present invention, a liquid mixture of a particular combination of the above-mentioned first and second primers, the DNA polymerase, and the liquid sample is used. The amounts of the first primer, the second primer, and the DNA polymerase can be varied depending on the species of the liquid sample, but may be easily determined in a range that the DNA amplification step may be carried out by the PCR method. The liquid mixture in some cases may contain a buffer solution (for example, a tris hydrochloride buffer solution), a stabilizing agent (for example, gelatine), or a salt (for example, sodium chloride).

According to the method of the present invention, the liquid mixture is used in the amplification cycle of the PCR method. The amplification cycle comprises steps of:

(i) denaturing a double-strand DNA (for about 10 seconds to 2 minutes at about 90° C. to 95° C.), (ii) annealing the single-strand DNA with the first and second primers (for about 30 seconds to about 3 minutes at about 37° C. to 70° C.), and (iii) extending a DNA by the DNA polymerase (for about 30 seconds to about 5 minutes at about 65° C. to 80° C.).

After each cycle, the DNA is amplified two-fold. Therefore, after n cycles of amplifications, the DNA is amplified $2^n$ fold. In the present invention, the above-mentioned amplification cycle is repeated 10 to 60 times, preferably 20 to 40 times. In the final cycle, it is preferable to extend the heating time of the step (iii) to about 5 to 10 minutes so as to complete the DNA synthesis.

By the above amplification cycle is completed, enough amounts of DNA about 200 to 300 bp are synthesized, if HSV is present in a sample. The resultant DNA is detected by the following DNA detection step.

For the DNA detection step, there may be used the method of utilizing gel electrophoresis and ethidium bromide dyeing; the Southern blotting hybridization method; or the method of determining the base sequence by the dideoxy method; the radioactive labeling method, or the like. When the gel electrophoresis method is used, it is possible to use, for example, submarine type electrophoresis using agarose gel as a carrier or slab gel electrophoresis using acrylamide.

For the Southern blotting hybridization or the in situ hybridization, it is possible to use a radioactive probe or a nonradioactive probes (for example, a probe labeled with an enzyme, biotin, digoxigenin, chemoluminescent substance or fluorescent substance).

Further, when the method of determining the base sequence by the dideoxy method is used, there may be used an automatic DNA sequencer (Applied Biosystems) using a fluorescent label.

The present invention also provides two types of DNA probes, specific to the HSV I DNA and HSV II DNA. Accordingly, the present invention also relates to a method of the type-specific detection of herpes simplex virus, characterized by bringing an oligonucleotide probe having at least 10 bases in a base sequence of the formula (3):

CCCCGATTCG GGCCCGGTCG CTCGCTACCG GTGCGCCACC (SEQ ID NO: 5) (3)

or the formula (4)

CCCCGCGGGC GCCGCCCCTC CCCCCGCGCG CCGCGGGCTG (SEQ ID NO: 6) (4)

and carrying a label thereon into contact with a sample; and detecting a signal from the label.

The base sequence of the formula (3) includes the 40 bases from the 139th base to 186th base downstream from the 5' end of the BamHIB fragment. The DNA probe containing an oligonucleotide having at least 10 bases in the base sequence of the formula (3) (hereinafter referred to optionally as the probe A) is specific to the BamHIB fragment of the HSV I DNA. The length of the probe varies with the kind of the pre-treatment applied to the sample. When the sample is treated by the DNA amplification step of the PCR method, the probe can be from 10 bp up to the size of the DNA fragment (except the primer part) amplified by the PCR merhod. Further, when the sample is not treated by the DNA amplification step of the PCR merhod, and the probe A is used for the in situ hybridization merhod, the length of the probe A may be of a size from 10 bp to 287 bp. The DNA probe A (40 mer) consisting of the oligonucleotide having 40 bases in the base sequence of the formula (3) is preferable, because such a DNA probe may be used for a sample after the treatment of the DNA amplification step of the PCR method or of the in-situ hybridization method. The probe A may be prepared by the method of using a succinoimide (for example, disuccinymidylsuberate), the maleimide method, the active halogen method, a photoreaction using an azide, or the carbodiimide method.

The base sequence of the formula (4) includes the 40 bases from the 147th base to the 187th base downstream from the 5' end of the a' sequence. A DNA probe containing an oligonucleotide having at least 10 bases in the base sequence of the formula (4) (hereinafter optionally referred to as the probe B) is specific to the a' sequence of the HSV II DNA. The length of the probe B varies with the kind of the pre-treatment of the sample. When the sample is treated by the DNA amplification step of the PCR method, the probe can be from 10 bp up to the size of the DNA fragment (except the primer part) amplified by the PCR method. Further, when the sample is not treated by the DNA amplification step of the PCR method, and the probe B is used for the in-situ hybridization method, the length of the probe B may be of a size from 10 bp to 185 bp. The DNA probe B (40 mer) consisting of the oligonucleotide having 40 bases in the base formula (4) in is preferable, because such a DNA probe may be used for a sample after the treatment of the DNA amplification step of the PCR method or of the in-situ hybridization method. The probe B may be prepared the same methods as those for preparing the probe A as mentioned above.

Any known substances may be used for labeling the probes A and B. Preferably, a nonradioactive substance (enzyme, fluorescent dye, luminescent substance, biotin, etc.) is used. For synthesizing the labeled DNA, there mainly are following two methods:

(1) the method of preparing a labeled DNA directly in the course of synthesizing a DNA, and
(2) the method of synthesizing a DNA with bonded linkers, then isolating the DNA, and applying a labeling agent thereto. Particularly, the method (2) is preferable because the kind of the labels can be easily changed dependently upon the usage, and thus the method (2) is superior in terms of application. As the linker used in the method (2), there may be mentioned 5'-dimethoxytolyl-5-[N-(trifluoroacetylaminohexyl)-3-acrylimide]-2'-deoxyuridine-3'-[(2-cyanoethyl)-(N,N-diisopropyl]]-phospholamidide etc. Any conventionally known methods may be used for generating a signal from the label bonded to the probe and measuring the signal.

When the combination of the primers (1a) and (2a) is used in the method of the present invention, the 243 bp base part corresponding to a part of the BamHIB fragment gene is amplified and synthesized in a specific manner, in a lot of amounts, and in a short time, only if the HSV I DNA is present in the sample. Further, when the combination of the primers (1b) and (2b) is used, the 212 bp base part corresponding to a part of the a' sequence gene is amplified and synthesized in a specific manner, in a large amount, and in a short time, only if the HSV II DNA is present in the sample. Therefore, it is possible to carry out a detection extremely specific to the HSV I virus and/or HSV II virus present in a sample. Further, the DNA is amplified and synthesized even when the HSV I DNA or the HSV II DNA is present in a sample in a slight amount, and so the sensitivity is high.

Further, a labeled DNA probe specific to the HSV I DNA or HSV II DNA (amplified in some cases) is used in the present invention, and therefore, it is possible to detect the HSV I DNA or the HSV II DNA extremely accurately. Further, if a combination of the amplification step using the first and second primers and the detection step using the above-mentioned probes is used, the time required for the detection is about 4 to 5 hours in the case of ethidium bromide dyeing and is about 48 to 50 hours even in the case of the Southern blotting hybridization method, and so the results can be obtained rapidly.

EXAMPLES

The present invention now will be further illustrated by, but is by no means limited to, the following Examples.

Example 1

Preparation of Primers and Probes

A primer (1α) having 20 bases in the sequence of the formula (1a) was synthesized by attaching an adenine CPG column to a Model 381A automatic DNA synthesizer (Applied Biosystems), a primer (2α) having 20 bases in the sequence of the formula (2a) was synthesized by attaching a thymine CPG column to the same, and a primer (1β) having 20 bases in the sequence of the formula (1b) and a primer (2β) having 20 bases in the sequence of the formula (2b) were synthesized by attaching a guanine CPG column to the same. A disposable syringe (2.5 ml) containing 2.5 ml of ammonia water (about 30%) was connected to the CPG column wherein the synthesis step was completed. The ammonia water was injected into the column, and the synthesized DNA fragments were eluted out. The vial containing the recovered DNA ammonia solution was plugged air-tightly and heated at 65° C. for 6 hours, then was cooled to room temperature, and then the solution was concentrated. The concentrate was lyophilized, dissolved in 10 mM triethyl ammonium acetate (hereinafter abbreviated as TEA-A) (pH 7.4), and then the precipitate was removed. A separation column (YMC-Pack ODS-AM313: YMC) was attached to a Type L-6200 high performance liquid chromatography apparatus (Hitachi) (hereinafter referred to as an HPLC), then purification was carried out using a concentration gradient by acetonitrile and 95 mM-TEA-A containing 5% acetonitrile, and the main peaks were collected. To the resultant residue, 80% acetic acid (adjusted by acetonitrile) was added to suspend the residue, then the suspension was allowed to stand at room temperature for 30 minutes, and dried under reduced pressure. The dried product was dissolved in 10 mM-TEA-A, extracted with diethylether, and dried under reduced pressure. The dried DNA sample was dissolved in TEA-A and the precipitate was removed. A second purification was carried out by a HPLC and the main peaks were collected. The resultant purified DNA primers were dried under reduced pressure to store, and used for the Examples 2 and 3.

By the same procedure as mentioned above, a probe a having 40 bases in the sequence of the formula (3) and a probe a having 40 bases in the sequence of the formula (4) were synthesized. For the synthesis of the probe a, a cytosine CPG column was used, and for the synthesis of the probe b, a guanine CPG column was used.

Example 2

Preparation of Labeled Probes (Oligo-labeling)

The probes a and b prepared in Example 1 were oligo-labeled by $^{32}P$ (using oligo-labeling kit of Pharmacia). To 4 µl of an aqueous solution containing 100 ng of the probe DNA, 58 µl of water was added. The whole was heated for 10 minutes at 100° C., then was immediately cooled with ice. To the ice-cooled probe solution, 20 µl of deoxynucleotide-triphosphate mixture, 4 µl of bovine serum albumin, 4 µl of Klenow enzyme, and 1 µl of $\alpha^{32}p$-dCTP (300 Ci) were added, then the whole was allowed to stand at room temperature for 2 hours. Then, 40 µl of the reaction terminator-solution, 40 µl of carrier RNA (10 mg/ml), and 360 µl of water were added. To the diluted reaction solution, 0.1 part by volume of 4M sodium chloride and 2 parts by volume of ethyl alcohol were added, then the whole was allowed to stand at −70° C. for 15 minutes to precipitate the DNA, and then was centrifuged at 15,000 rpm. The resultant precipitate was dissolved in 30 µl of a 10 mM tris hydrochloride buffer solution containing 1 mM-EDTA, then 16 µl of 7.5M ammonium acetate and 92 µl of ethyl alcohol were added, and the whole was allowed to stand at −70° C. for 15 minutes, then was centrifuged. To the resultant precipitate, 200 µl of 75% ethyl alcohol was added, then the whole was further centrifuged, and the resultant precipitate was air-dried at room temperature for 2 hours. The resultant labeled probe was dissolved in 200 µl of a 10 mM tris hydrochloride buffer solution containing 1 mM-EDTA. The resultant labeled probe solution was used in an amount of about 10 µl for a single dot blotting.

Example 3

Preparation of Labeled Probe (End-Labeling)

A probe end-labeled with $^{32}P$ was prepared by the following method: To 1 µl of a solution containing 500 ng of the probe DNA prepared in Example 1, 2.5 µl of a 10×kinase buffer solution, 1.5 µl (15 units) of T4 polynucleotide kinase, and 20 µl (200 Ci) of $\gamma$-$^{32}P$-dATP were added, then the mixture was held at 37° C. for 45 minutes. After 400 µl of a solution (1 mM-EDTA-1M tris hydrochloride buffer solution containing 140 µl of triethylamine in 100 ml of 0.1M tris-HCl; pH 7.7; hereinafter referred to as the solution A) was added to the reaction solution, the whole was passed through a reverse phase ion exchange column (NEN SORB 20 column: Du Pont) which had been washed by 2 ml of methyl alcohol and 2 ml of the solution A. After the column was washed with 3 ml of the solution A and 3 ml of water, then the labeled probe was eluted by 1 ml of a 20% ethyl alcohol aqueous solution. The labeled probe was eluted in the first 500 µl fraction. For a single hybridization, 50 µl of the eluent was used.

Example 4

Extraction of HSV DNA

In this Example, there were used WT51-3-4 [strain isolated from a herpetic keratitis patient: *Acta Virol.* 23: 226–230 (1979)] as the standard strain of HSV I, UW268 as the standard strain of HSV II, and five strains for each of Type I and Type II of clinically isolated strains (isolated from herpes-like sites of patients infected with HSV) as the HSV wild strains which had been determined as to the types.

Each virus was made to infect CV-1 cells derived from the kidney of African green monkeys at a concentration of 1 pfu/cell. The cells infected with viruses were cultivated in a gaseous phase of 5% carbon dioxide and 95% air. The cells showing effects of cell modification were used to extract the virus DNA's by the sucrose method (*Virology*, 93, 260–264, 1979).

Example 5

Amplification of HSV-DNA by PCR Method

Ten (10) ng amounts of each of DNA's extracted in Example 4 of the HSV I and II standard strains and the HSV wild strains which had been determined as to the types were added to 100 µl of a PCR reaction solution containing 125 µM-dATP, 125 µM-dCTP, 125 µM-dTTP, 31.25 µM-dGTP, 93.75 µM deaza-$C^7$-GTP (hereinafter abbreviated as $dC^7dGTP$), 0.01% gelatine, 20 mM tris hydrochloride buffer solution (pH 8.8), 1.5 mM-MgCl$_2$, 50 mM-KCl, 10% dimethylsulfoxide, 2 µM primer, and 2.5 units of Taq polymerase (AmpliTaq DNA polymerase: Cetus). For the specimen using the HSV I primer, the PCR method was carried out to amplify the DNA by repeating 30 times the cycle consisting of (i) 92° C. for 1 minute, (ii) 60° C. for 1 minute, and (iii) 72° C. for 2 minutes, and finally treating at 72° C. for 5 minutes. For the specimen using the HSV II primer, the PCR method was carried out to amplify the DNA by repeating 30 times the cycle consisting of (i) 93° C. for 1 minute, (ii) 65° C. for 1 minute, and (iii) 73° C. for 1 minute, and finally treating at 73° C. for 5 minutes.

Example 6

Examination and Diagnosis of PCR Reaction Product by Electrophoresis

Figure 2:
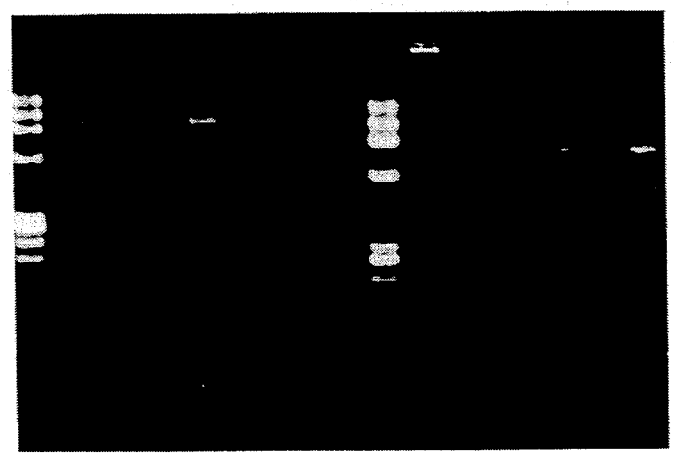
FIG. 2 shows the results of electrophoresis relating to DNAs amplified by a PCR using the HSV II primer of the present invention.

Electrophoresis gel was prepared by dissolving 4% agarose gel in 1 liter of a buffer solution (pH 8.0) containing 5.4 g of tris hydrochloride, 2.75 g of boric acid and 2 ml of 0.5M EDTA (hereinafter referred to as 0.5×TBE) and pouring into a gel plate of Mupid (Advance). Then, 2 μl of a 15% aqueous solution of Ficoll Type 400 (Pharmacia) was mixed with 10 μl of the solution after the PCR reaction, and the mixture was inserted into sample wells. After 1×TBE was inserted into an electrode tank, electrophoresis was carried out at room temperature and 100 V for 2 hours. After the electrophoresis was completed, the agarose gel was stained with ethidium bromide and the results of the electrophoresis were observed under illumination from a UV illuminator. The results of the case wherein the HSV I primer was used are shown in FIG. 1 and the results of the case wherein the HSV II primer was used are shown in FIG. 2. In FIGS. 1 and 2, the reference numerals have the following meanings:

M: DNA markers,
1: HSV I standard strain (WT51-3-4),
2-6: HSV I wild strains,
7: HSV II standard strain (UW268),
8-12: HSV II wild strains.

As the DNA markers ($\phi$×174-HaeIII digest), those appearing at 72 bp, 118 bp, 194 bp, 234 bp, 271 bp, 281 bp, 310 bp, 603 bp, 872 bp, 1078 bp, and 1357 bp from the bottom were used. It is manifest from FIGS. 1 and 2 that the PCR method wherein the primers according to the present invention are used make it possible to amplify the particular DNA parts specific to the desired HSV's.

As shown in the ethidium bromide dyeing of FIG. 2, plural bands are observed at HSV I and HSV II in the PCR method wherein the HSV II primers are used. Because the amplified parts are different from each other in the HSV I and HSV II, it is possible to determine the HSV I and HSV II by making comparison with the standard strains thereof. Further, to confirm the above, Southern hybridization was carried out using the end-labeled probes a and b prepared in Example 3. Namely, autoradiography was obtained after hybridization with the each probe and the Southern blottings on the DNA hybridization membrane (Gene Screen Plus: Du Pont) from the agarose gel after electrophoresis. The results are shown in FIG. 3. The lanes 1 and 3 of FIG. 3 are HSV I standard strain (WT51-3-4) and the lanes 2 and 4 are HSV II standard strain (UW268). Further, the end-labeled probe a was used for the lanes 1 and 2 of FIG. 3, while the end-labeled probe b was used for the lanes 3 and 4. It is manifest from FIG. 3 that only the bands amplified by the HSV II primers as a template were hybridized with the probe b for determining HSV II, while the bands amplified by the HSV I primers as a template were not hybridized with the probe b for determining HSV II. As apparent from the above results, it is possible to determine and diagnose whether the virus causing the HSV infection is the HSV I or the HSV II, by amplifying the DNA in the patient samples by the primers of the present invention and examining the amplified DNA by the probes of the present invention.

Example 7

Determination of HSV Types by Dot Blotting of Blister Solution

A bulla (5 μl) taken from patients suspected of having herpes infection was suspended in 2 ml of a physiological saline solution for dilution. To 200 μl of the diluted sample, the same amount of 0.5N NaOH was added and the mixture was allowed to stand at room temperature for 10 minutes. The resultant treated sample (50 μl) containing the modified DNA was placed on a blotting apparatus having Gene Screen Plus NEF976 (Du Pont) and allowed to stand at room temperature for 30 minutes, then the liquid was removed by suction. The Gene Screen Plus NEF976 with the blotted DNA was placed in a plastic bag, then 5 ml of a hybridization solution containing a composition of 0.2% polyvinylpyrrolidone (molecular weight of 40,000), 0.2% Ficoll (molecular weight of 40,000), 0.2% bovine serum albumin, 0.05M tris hydrochloride buffer solution (pH 7.5), 1M sodium chloride, 0.1% sodium phosphate, 1% sodium lauryl sulfate, 10% dextran sodium sulfate (molecular weight of 500,000), and modified salmon sperm DNA (100 μg/ml) was added thereto and the bag was sealed airtightly. The whole was allowed to stand at 65° C. for 6 hours, then the $^{32}$P-labeled and HSV-determining probes prepared in Example 2 (oligo labeling) were added, then the whole was allowed to further stand at 65° C. for 6 hours. The treated Gene Screen Plus NEF976 was washed twice at room temperature with agitation for 5 minutes in a 2×SSC (pH 7.0) containing a large amount of 0.3M sodium chloride and 0.034M trisodium citrate, then was washed twice at 65° C. for 15 minutes in a 2×SSC and 1% SDS, further was washed twice at room temperature with agitation for 5 minutes in 0.1×SSC. The washed film was air-dried at room temperature for 1 hour.

The Gene Screen Plus NEF976 which was subjected to the hybridization treatment with the HSV type-determining probes was placed in an exposing cassette and fixed therein. Then the film (Kodak-X-OMAT-AR XAR5) was exposed at −70° C. and developed. The results are shown in FIG. 4. In FIG. 4, 1 to 5 are patient samples, 6 is an HSV I standard strain, and 7 is an HSV II standard strain. The remarks at the right side of the figure are the results of determination. As apparent from FIG. 4, the probe a hybridizes with the HSV I virus and the probe b hybridizes with the HSV II virus.

Example 8

Type Determination of HSV in Bulla (1) The bulla (5 μl) used in Example 7 was suspended in 2 ml of physiological saline solution. To 50 μl of the diluted sample, 50 μl of 6M guanidine isocyanate and 10 μl of glass powder were added, and the mixture was allowed to stand at room temperature. After 10 minutes, the mixture was centrifuged at 15,000 rpm for 2 minutes, and the supernatent was discarded. To the precipitate, 1 ml of a 10 mM tris-hydrochloride buffer solution (pH 7.4) containing 50% ethyl alcohol, 1 mM-EDTA, and 50 mM sodium chloride was added to prepare a suspension. The suspension was agitated, then centrifuged further at 15,000 rpm for 2 minutes. The washing of the glass powder by the centrifugation was repeated three times. To the washed glass powder, 50 μl of distilled water was added to prepare a suspension, then the suspension was allowed to stand at 55° C. for 15 minutes. Then, the suspension was centrifuged at 15,000 rpm for 2 minutes. The supernatent was used as the DNA extract solution for the DNA amplification process by the PCR method. The DNA amplification process was carried out by the procedure as described in Example 5 and the type determination of the PCR reaction product was carried out by the procedure as described in Example 6.

(2) As a control test, the conventional fluorescent antibody method was carried out. Namely, diseased areas were rubbed with a small cotton swab and the resultant substance was applied at two points on a nonfluorescent slide. The slide was allowed to dry naturally, and immobilized with acetone at room temperature for 10 minutes. Then, the immobilized samples were reacted at room temperature for about 30 minutes with a fluorescently labeled anti-HSV-I antibody (Syva) or anti-HSV-II antibody (Syva). The slide glass was rinsed, then buried in glycerine, and observed under a fluorescence microscope.

(3) Further, as a control test, the conventional clinical diagnosis method (wherein a doctor made the diagnosis by observing the diseased areas and lesions) was carried out. The results are shown in the following Table 1.

TABLE 1

| Method of examination | HSV-I | HSV-II | Examination not possible | Determination not possible |
|---|---|---|---|---|
| PCR method | 12 | 6 | 0 | 0 |
| Fluorescent antibody method | 7 | 1 | 8 | 2 |
| Clinical examination | 3 | 3 | — | 12 |

The above Table 1 shows that, according to the clinical examination method as to the 18 bulla solutions, three samples were found to be HSV I, three samples were found to be HSV II, and 12 samples were not able to determine (it was not able to conclusively diagnosis them as being Type I or Type II). By the fluorescent antibody method, seven samples were found to be HSV I, one sample HSV II, eight samples were not able to examine (diseased cells were not able to take up), and two samples were not able to determine. On the other hand, by the dot blot hybridization DNA examination according to the present invention, 12 samples were found to be HSV I and six HSV II. No samples could not be examined or could not be determined as to the types.

Example 9

Type Determination of HSV of Throat Swab

By carrying out the procedure as described in Example 8 (1), DNA was extracted from the throat swab of patients suspected of suffering from herpes infection. The extracted DNA was used for the type determination of HSV by the dot blot method as described in Example 7 and the PCR method as described in Example 8 (1). Among the 36 examined throat swab, the dot blot method showed that 10 samples were HSV I, 10 samples could not be determined as to the type, and 16 samples were negative. The PCR method according to the present invention, however, exhibited a high ability to the type determination, wherein 32 samples found to be HSV I and the remaining four negative. The results are shown in Table 2.

TABLE 2

| Method of examination | Total number of samples | HSV-I | HSV-II | Determination impossible | Negative |
|---|---|---|---|---|---|
| Dot blot method | 36 | 10 | 0 | 10 | 16 |
| PCR method | 36 | 32 | 0 | 0 | 4 |

As above, the present invention was explained with reference to particular embodiments, but modifications and improvements obvious to those skilled in the art are included in the scope of the present invention.

INDUSTRIAL APPLICABILITY

The process of the present invention provides primers which can be used for the amplification of DNA fragments specific to HSV I DNA or HSV II DNA, and also provides, as probes specific to HSV I DNA or HSV II DNA, oligonucleotides having base sequences of a size to an extent that can be chemically synthesized and further which are not reduced in type-specificity. Therefore, it is possible to determinate infection of HSV I or HSV II rapidly in a type-specific manner at a high precision, and also possible to make use of the results thereof in diagnosis and treatment.

We claim:

1. In a method of detecting herpes simplex virus a aqueous liquid sample, including the sequential steps of:
  (I) amplifying DNA in a mixture containing said aqueous liquid sample, a DNA polymerase and a combination of primers, and
  (II) detecting and analyzing amplified DNA from step (I), the improvement which comprises using as said combination of primers:
    (a) a first combination of a first BamHIB oligonucleotide primer containing at least 15 consecutive bases of the nucleotide sequence

CACGGGTATA AGGACATCCA (SEQ ID NO: 1)

with a second BamHIB oligonucleotide primer containing at least 15 consecutive bases of the nucleotide sequence

GGGTCCTCGT CCAGATCGCT (SEQ ID NO: 2)

to amplify a 243 base pair fragment of the BamHIB DNA fragment of herpes simplex virus type I,
    (b) a second combination of a first a' oligonucleotide primer containing at least 15 consecutive bases of the nucleotide sequence

GCCTCTTTTC CCCCGGGGAG (SEQ ID NO: 3)

with a second a' oligonucleotide primer containing at least 15 consecutive bases of the nucleotide sequence

GGGAAAAAAG CCGCGCCGGGG (SEQ ID NO: 4)

to amplify a 212 base pair fragment of the a' DNA sequence of herpes simplex virus type II, or,
  (c) both said first combination (a) and said second combination (b).

2. The method according to claim 1, wherein said first combination of primers is used and said first BamHIB primer is a 20 mer to 25 mer.

3. The method according to claim 1, wherein the BamHIB DNA fragment of herpes simplex virus type I is amplified.

4. The method according to claim 3, wherein in said first combination of primers said first BamHIB primer has the nucleotide sequence of SEQ ID NO: 1.

5. The method according to claim 1, wherein said first combination of primers is used and said second BamHIB primer is a 20 mer to 25 mer.

6. The method according to claim 3, wherein said second BamHIB primer has the nucleotide sequence of SEQ ID NO.2.

7. The method according to claim 1, wherein said second combination of primers is used and said first a' primer is a 20 mer to 25 mer.

8. The method according to claim 1, wherein the a' DNA sequence of herpes simplex virus type II is amplified.

9. The method according to claim 8, wherein in said second combination of primers said first a' primer has the nucleotide sequence of SEQ ID NO:3.

10. The method according to claim 8, wherein in said second combination of primers said second a' primer is a 20 mer to 25 mer.

11. The method according to claim 8, wherein in said second combination of primers said second a' primer has the nucleotide sequence of SEQ ID NO:4.

12. The method according to claim 1 further comprising the steps of
  (i) denaturing double stranded DNA to obtain single stranded DNA,
  (ii) annealing single stranded DNA from step (i) with a first and second primer, and
  (iii) extending the annealed DNA from step (ii) using a DNA polymerase.

13. The method according to claim 1, wherein in step (II) amplified DNA is analyzed by gel electrophoresis, ethidium bromide staining, Southern hybridization, dideoxy sequencing or radioactive labeling.

14. The method according to claim 1, wherein step (II) further comprises the steps of
  (i) contacting the mixture of step (I) with an oligonucleotide probe selected from the group consisting of a BamHIB oligonucleotide probe specific to a region of the BamHIB DNA fragment of herpes simplex virus type I, said probe having a nucleotide sequence containing at least 10 contiguous bases of the sequence:

CCCCGATTCG GGCCCGGTCG CTCGCTACCG GTGCGCCACC (SEQ ID NO: 5)

and carrying a label thereon, an a' oligonucleotide probe specific to a region of the a' DNA sequence of herpes simplex virus type II, said a' probe having a nucleotide sequence containing at least 10 contiguous bases of the sequence:

CCCCGCGGGC GCCGCCCCTC CCCCCGCGCG CCGCGGGCTG (SEQ ID NO: 6)

and carrying a label thereon, and combinations thereof; and
  (ii) detecting a signal from said label.

15. The method according to claim 14, wherein said oligonucleotide probe is a BamHIB probe.

16. The method according to claim 14, wherein said oligonucleotide probe is an a' probe.

17. The method according to claim 1, wherein the oligonucleotide primers are 15 mers to 30 mers.

* * * * *

UNITED STATES PATENT AND TRADEMARK OFFICE
CERTIFICATE OF CORRECTION

PATENT NO.   : 5,354,653
DATED        : October 11, 1994
INVENTOR(S)  : Toshiya MATSUMOTO, Takashi KURIMURA, Hiroshi KITA It is certified that error appears in the above-indentified patent and that said Letters Patent is hereby corrected as shown below:

Column 3, line 25, change "48st" to --481st-- and change "482nd" to --462nd--.

Column 5, line 11, change "139th" to --319th-- and change "186th" to --358th--.

Column 15:

Claim 1, line 1, change "In a" to --A-- and after "virus" delete "a" and insert --in an--.

Signed and Sealed this

Eighteenth Day of April, 1995

BRUCE LEHMAN

*Commissioner of Patents and Trademarks*

*Attest:*

*Attesting Officer*

SEQUENCE LISTING ( 1 ) GENERAL INFORMATION:

( i i i ) NUMBER OF SEQUENCES:6

( 2 ) INFORMATION FOR SEQ ID NO: 1:

( i ) SEQUENCE CHARACTERISTICS:
        ( A ) LENGTH:20 nucleotides
        ( B ) TYPE:nucleic acid
        ( C ) STRANDEDNESS:single
        ( D ) TOPOLOGY:linear ( i i ) MOLECULE TYPE:Oligonucleotide ( i i i ) HYPOTHETICAL:no ( i v ) ANTI-SENSE:no ( i x ) FEATURE:
        ( A ) NAME/KEY:Primer 1a ( x i ) SEQUENCE DESCRIPTION:SEQ ID NO: 1:
CACGGGTATA AGGACATCCA                  20

( 2 ) INFORMATION FOR SEQ ID NO: 2:

( i ) SEQUENCE CHARACTERISTICS:
        ( A ) LENGTH:20 nucleotides
        ( B ) TYPE:nucleic acid
        ( C ) STRANDEDNESS:single
        ( D ) TOPOLOGY:linear ( i i ) MOLECULE TYPE:oligonucleotide ( i i i ) HYPOTHETICAL:no ( i v ) ANTI-SENSE:no ( i x ) FEATURE:
        ( A ) NAME/KEY:Primer 2a ( x i ) SEQUENCE DESCRIPTION:SEQ ID NO: 2:
GGGTCCTCGT CCAGATCGCT                  20

( 2 ) INFORMATION FOR SEQ ID NO: 3:

( i ) SEQUENCE CHARACTERISTICS:
        ( A ) LENGTH:20 nucleotides
        ( B ) TYPE:nucleic acid
        ( C ) STRANDEDNESS:single
        ( D ) TOPOLOGY:linear ( i i ) MOLECULE TYPE:oligonucleotide ( i i i ) HYPOTHETICAL:no ( i v ) ANTI-SENSE:no ( i x ) FEATURE:
        ( A ) NAME/KEY:Primer 1b ( x i ) SEQUENCE DESCRIPTION:SEQ ID NO: 3:
GCCTCTTTTC CCCCGGGGAG                  20

( 2 ) INFORMATION FOR SEQ ID NO: 4:

( i ) SEQUENCE CHARACTERISTICS:
        ( A ) LENGTH:21 nucleotides
        ( B ) TYPE:nucleic acid
        ( C ) STRANDEDNESS:single
        ( D ) TOPOLOGY:linear ( i i ) MOLECULE TYPE:oligonucleotide ( i x ) FEATURE:
        ( A ) NAME/KEY:Primer 2b ( x i ) SEQUENCE DESCRIPTION:SEQ ID NO: 4:
GGGAAAAAAG CCGCGCCGGG G                21

( 2 ) INFORMATION FOR SEQ ID NO: 5:

( i ) SEQUENCE CHARACTERISTICS:
        ( A ) LENGTH:40 nucleotides
        ( B ) TYPE:nucleic acid
        ( C ) STRANDEDNESS:single
        ( D ) TOPOLOGY:linear ( i i ) MOLECULE TYPE:oligonucleotide ( i x ) FEATURE:
        ( A ) NAME/KEY:HSV Probe of the formula (3)

( x i ) SEQUENCE DESCRIPTION:SEQ ID NO: 5:
CCCCGATTCG GGCCCGGTCG CTCGCTACCG GTGCGCCACC    40

( 2 ) INFORMATION FOR SEQ ID NO: 6:

( i ) SEQUENCE CHARACTERISTICS:
        ( A ) LENGTH:40 nucleotides
        ( B ) TYPE:nucleic acid
        ( C ) STRANDEDNESS:single (D) TOPOLOGY: linear (ii) MOLECULE TYPE: oligonucleotide (ix) FEATURE:
  (A) NAME/KEY:HSV Probe of the formula (4)

(xi) SEQUENCE DESCRIPTION:SEQ ID NO: 6:

CCCCGCGGGC GCCGCCCCTC CCCCCGCGCG CCGCGGGCTG    40